(12) United States Patent  
Debbas

(10) Patent No.: US 6,939,356 B2
(45) Date of Patent: Sep. 6, 2005

(54) MEDICAL INSTRUMENT FOR CLOSURE OF TROCAR SITE OPENINGS AND METHOD FOR USE OF SAME

(76) Inventor: Elie G. Debbas, 11701 Livingston Rd., Suite 201, Fort Washington, MD (US) 20744

( * ) Notice: Subject to any disclaimer, the term of this patent is extended or adjusted under 35 U.S.C. 154(b) by 548 days.

(21) Appl. No.: 10/156,114

(22) Filed: May 29, 2002

(65) Prior Publication Data

US 2003/0171764 A1 Sep. 11, 2003

Related U.S. Application Data

(60) Provisional application No. 60/361,701, filed on Mar. 6, 2002.

(51) Int. Cl.[7] ............................................... A61B 17/04
(52) U.S. Cl. ....................................... 606/144; 606/139
(58) Field of Search ................................ 606/139, 144, 606/145, 147, 148

(56) References Cited

U.S. PATENT DOCUMENTS

| | | | | |
|---|---|---|---|---|
| 5,320,632 A | * | 6/1994 | Heidmueller | 606/144 |
| 5,368,601 A | * | 11/1994 | Sauer et al. | 606/144 |
| 5,374,275 A | * | 12/1994 | Bradley et al. | 606/144 |
| 5,817,108 A | * | 10/1998 | Poncet | 606/139 |
| 5,868,762 A | * | 2/1999 | Cragg et al. | 606/144 |
| 6,743,241 B2 | * | 6/2004 | Kerr | 606/144 |

* cited by examiner

*Primary Examiner*—Julian W. Woo
(74) *Attorney, Agent, or Firm*—Birch, Stewart, Kolasch & Birch, LLP

(57) ABSTRACT

A medical instrument used for closing an opening for surgery in which a trocar is used, and a method of securely closing the opening. The instrument includes a hollow tube, into which is inserted an elongated actuating mechanism, having at least two needles that can be positioned in a closed or an open position. By securing a suture on the needles, inserting the instrument into the surgical opening, placing the needles into the open position, withdrawing the instrument through the body tissue, and tying the sutures, a secure closure of the surgical opening can be achieved.

19 Claims, 8 Drawing Sheets

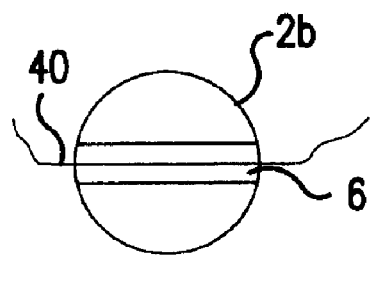
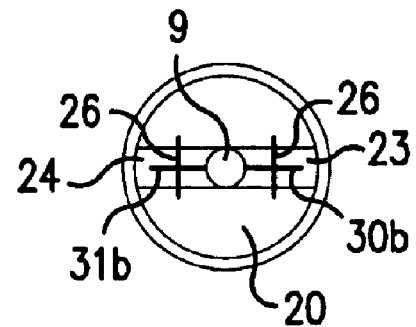
FIG.2a          FIG.2b
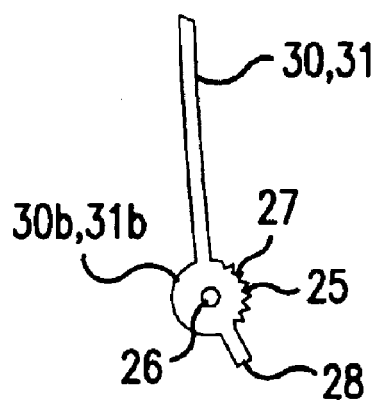
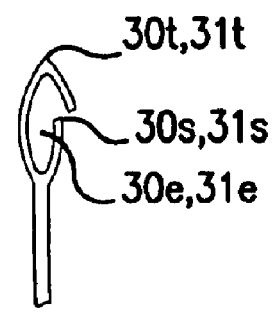
FIG.2c          FIG.2d

MEDICAL INSTRUMENT FOR CLOSURE OF TROCAR SITE OPENINGS AND METHOD FOR USE OF SAME

CROSS REFERENCE TO RELATED APPLICATIONS

This application claims priority to Provisional Application No. 60/361,701 filed on Mar. 6, 2002, the entire contents of which are incorporated by reference.

BACKGROUND OF THE INVENTION

1. Field of the Invention

The present invention relates to a medical instrument for closing an opening for surgery in which a trocar is used, and a method of securely closing the opening.

2. Description of Background Art

Conventionally, the closing of openings created by trocars of size No. 10 or larger has posed significant problems in surgery. Typically, conventional devices have one needle. In obese patients in particular, these devices are difficult, tedious, time consuming, and sometimes impossible to use. Also, when these conventional devices are used, many steps are required, which both complicates and increases the cost of the surgical procedure.

Specifically, since these conventional devices have only one needle, they require the passage of one suture at a time and the placement of sutures at varying distances from the peritoneal and fascial tissue edges. This often results in a poor or inadequate closure of the surgical opening. Also, since the use of conventional closure devices takes considerable time, the patient is subject to an unnecessary prolongation of anesthesia.

SUMMARY AND OBJECT OF THE INVENTION

The object of the present invention is to solve these problems, by providing a device that ensures accurate placement of the suture needles, and allows the surgeon to easily and accurately close a trocar site opening in a minimum of time.

To overcome the disadvantages of conventional devices and methods for closing an opening in which a trocar is used for surgery, the present invention provides an elongated hollow cylindrical member or tube for receiving an elongated actuating mechanism of approximately the same length as the cylindrical member. The elongated hollow cylindrical member has a proximal end top end, which is open, and a blunt distal end which is closed. Additionally, the hollow cylindrical member has longitudinal slots formed on opposite sides of the shaft of the cylindrical member, the two slots running longitudinally for predetermined distances between a point near the proximal end of the cylindrical member to a second point near the distal end of the cylindrical member. These longitudinal slots, or cuts through the outer surface of the cylindrical member, expose the inside of the cylindrical member to the outside. The longitudinal slots also are the openings through which needles (described below) are deployed during the use of the instrument.

The cylindrical member also has a slot on its distal end, but unlike the longitudinal slots, the distal end slot does not cut through to the inside of the cylindrical member. The slots running longitudinally are separate from the slot on the distal end of the cylindrical member.

An elongated actuating mechanism having a turnable shaft with a proximal end and a distal end is provided for insertion into the hollow cylindrical member during assembly of the medical instrument of the present invention. On the proximal end of the turnable shaft is a knurled knob for easy rotation of the shaft by hand. The shaft of the elongated actuating mechanism is formed with a screw-threaded portion formed near the distal end thereof.

During assembly of the medical instrument of the present invention, the shaft is inserted into the hollow cylindrical member or tube, and slides through an upper cylindrical holding piece which is affixed on the inside of the cylindrical member near the proximal end of the longitudinal slots. As the shaft is inserted further, the screw threaded portion at the distal end of the shaft engages with teeth formed on an arc portion of the distal end of each of two needles rotatably mounted in slots cut into upper edges of a lower cylindrical holding piece which is affixed on the inside of the hollow cylindrical member near the distal ends of the longitudinal slots. The spaces and the distal ends of the needles are aligned to face the slots in the cylindrical member. In other words, the plane of the distal ends of the needles pass through the open longitudinal slots formed on opposite sides of the cylindrical member. As such, the teeth formed on the arc portions of the needles engage the screw-threaded portions of the shaft.

The turnable shaft is insertable into the cylindrical member and through the cylindrical holding pieces. When inserted, the shaft is held in place with respect to the cylindrical member by the cylindrical holding pieces, the holding pieces fitting snuggly around the shaft.

The tips on the proximal ends of the needles are sharp permitting the needles to easily pass through tissue, whereas the sides along the lengths of the needles are provided with non-cutting surfaces.

The needles of the present invention can be manufactured in a variety of lengths to provide for closing openings in tissues of different thicknesses. Short needles are suitable for tissue having little thickness, whereas longer needles are needed to close a tissue having a large thickness, such as in obese patients. Accordingly the needles of the medical instrument of the present invention may be formed with lengths in the range of 2.0 to 20 cm or 0.75 to 8 inches, preferably 2.5 to 7.5 cm or 1 to 3 inches.

In an initial or closed position, the needles are arranged lengthwise along the length of the turnable shaft, and facing the longitudinal slots of the hollow tube. The length of the needles is less than the length of the slots, such that when the shaft is turned by means of the knob, the upper ends of the needles radiate outward through the longitudinal slots for a predetermined distance, in the range of 0.5 to 2.0 cm. By means of this turning, as described above, the needles can be positioned in either of two positions: a closed position, wherein the needles are pulled in close to the shaft, and an open position, wherein the proximal ends of the needles project outward for a predetermined distance.

An eye is formed near the proximal end of each needle, and each eye has a spring mechanism for easy loading of the suture. Prior to use of the instrument, a length of suture is threaded through the eye of one needle, down around the length of the hollow cylindrical members and through the slot at the distal end of the hollow cylindrical member, and then up the opposite side of the cylindrical member and through the eye of the other needle. Once the suture is threaded as described above, and the needles are turned to a closed position, the instrument is ready for insertion into the patient.

According to the present invention, an instrument for closure of surgical openings in which a trocar is used, includes an elongated hollow cylindrical member, an elongated actuating mechanism insertable into the hollow cylindrical member, the actuating mechanism including a turnable shaft, a pair of needles, the distal end of the needles being rotatably mounted on pins in slots in the lower cylindrical holding piece disposed inside the hollow cylindrical member near the distal end. The proximal ends of the needles are provided with eyes capable of being threaded with suture, and the needles can be positioned in either an open position or a closed position by turning the elongated shaft, thereby causing the needles of the instrument to move between the open and closed positions.

Further according to the present invention, a method for closing a surgical opening employing a medical instrument having a hollow cylindrical member, an actuating mechanism having a turnable shaft, and a pair of elongated needles which are rotatable, includes the steps of threading a suture through the tips of the needles and through an end slot of the hollow cylindrical member, placing the medical instrument into a closed position, inserting the medical instrument until tips of needles are below an inner most layer of tissue, deploying needles to an open position by turning a knob on a proximal end of the elongated shaft by a predetermined amount, withdrawing the medical instrument until tips of the needles appear above the skin level, removing the suture from the needles, reinserting the medical instrument while still in an open position until the tips of the needles are below the inner most layer of tissue, closing the instrument by turning the knob on the shaft, withdrawing the instrument, retrieving ends of the suture in a subcutaneous tissue; and tying required knots in the suture, thereby closing the surgical opening.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2(a) is a view of the instrument as viewed from the distal end, FIG. 2(b) shows a cross-sectional view of the distal end of the needles and a lower cylindrical holding piece taken at line II—II of FIG. 1(b), FIG. 2(c) is a side view of the arc portion on the distal end of the needle, and FIG. 2(d) is a side view of the eye of the needle showing the spring mechanism;

DETAILED DESCRIPTION OF THE PREFERRED EMBODIMENTS

Figure 1B:
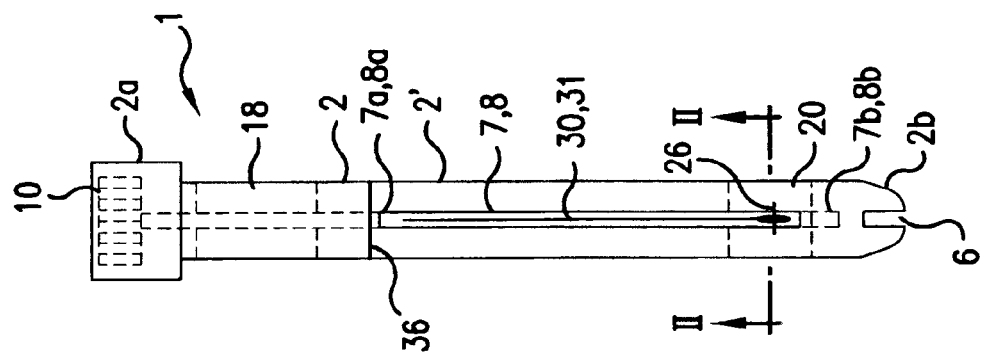
FIG. 1(b) is a side view of the instrument as viewed from the direction of the arrow in FIG. 1(a)
Figure 1A:
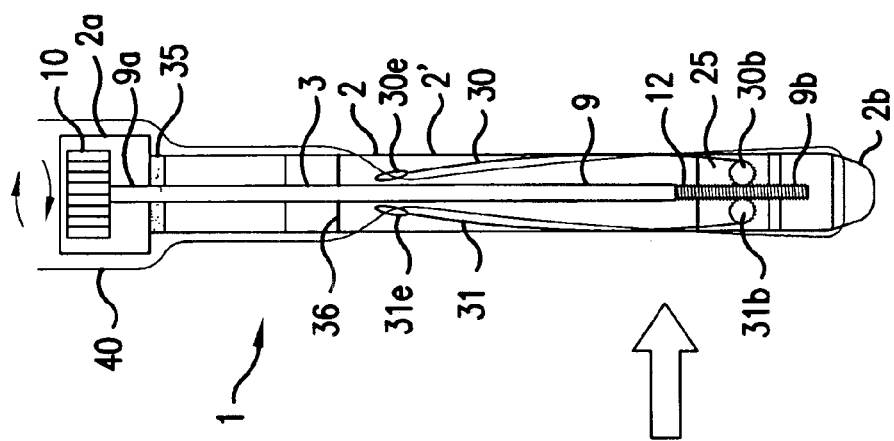
FIG. 1(a) is a sectional side view of the instrument of the present invention in a closed position.
Figure 3:
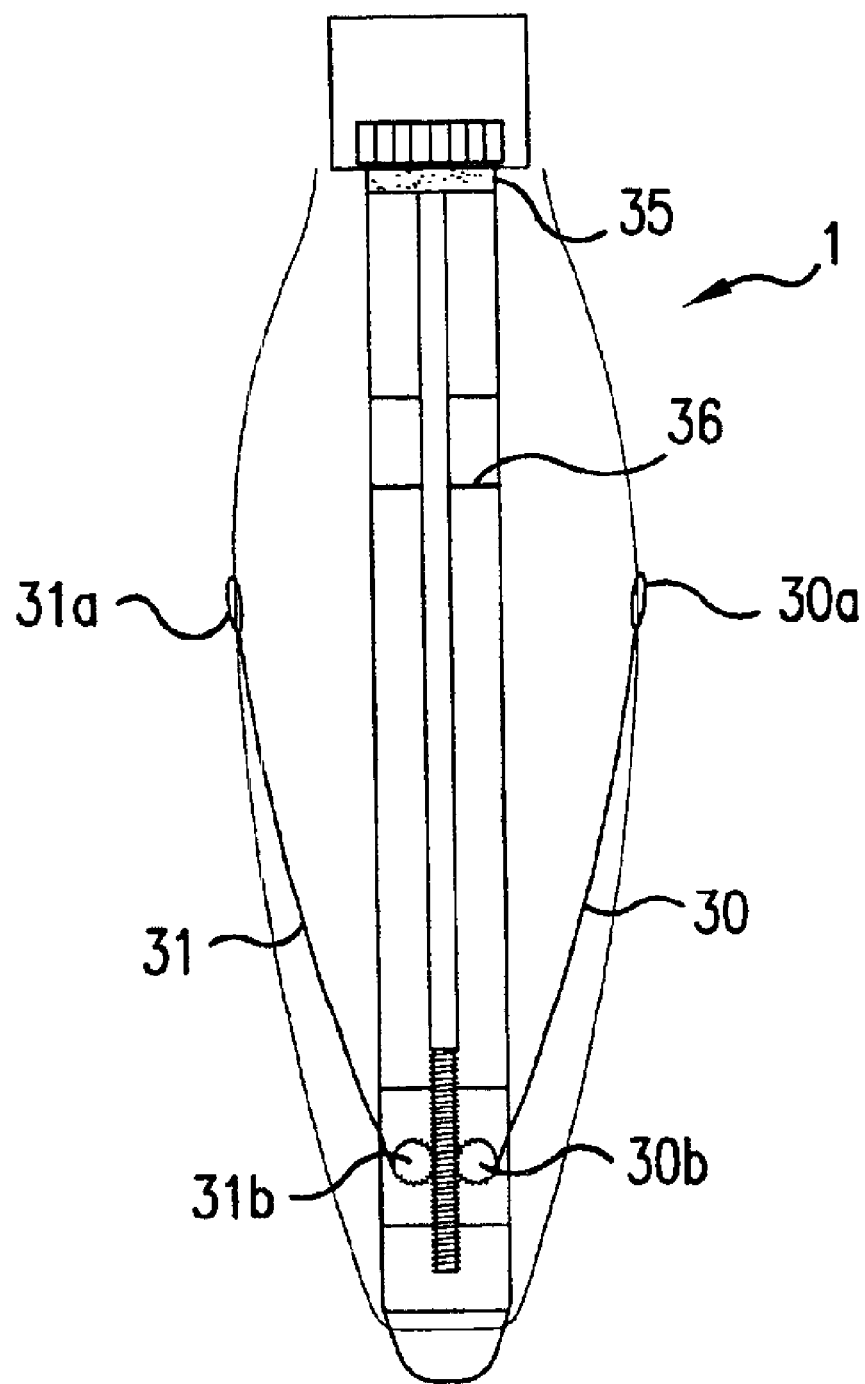
FIG. 3 is a sectional side view of the instrument of the present invention in an open position, viewed from the same direction as FIG. 1(a)

The first embodiment will be described with reference to FIGS. 1–3.

The medical instrument 1 for closing an opening for surgery includes an elongated hollow cylindrical member or tube 2 for receiving an elongated actuating mechanism 3 of approximately the same length as the tube 2. The elongated hollow cylindrical member or tube 2 has an outer surface 2', a proximal end 2a which is open, and a distal end 2b which is closed. The hollow cylindrical member 2 has longitudinal slots or cuts 7, 8 formed on opposite sides of the tube, the two slots 7, 8 running longitudinally for predetermined distances between a point near the proximal end 2a to a second point near the distal end 2b. These longitudinal slots 7, 8 cut through the outer surface 2' of cylindrical member 2, and expose the inside of the cylindrical member to the outside. The cylindrical member also has a slot 6 on its distal end, but unlike the longitudinal slots 7, 8, the distal end slot 6 doses not cut through the closed distal end 2b of the cylinder member 2. Slot 6 is shown in FIGS. 1(b) and 2(a). The longitudinal slots 7, 8 are separate from the end slot 6.

The elongated actuating mechanism having a turnable shaft 9 with a proximal end 9a and a distal end 9b is provided for insertion into the hollow tube. On the proximal end of the turnable shaft 9 is a knurled knob 10 for easy rotation of the shaft by hand. The shaft of the elongated actuating mechanism is formed with screw-threaded portion 12 formed near the distal end 9b thereof.

During assembly of the medical instrument of the present invention, shaft 9 is inserted into the hollow tube 2, and slides through the upper holding piece 18 which is affixed on the inside of the hollow tube 2 near the proximal ends 7a, 8a of the longitudinal slots 7, 8. As the shaft is inserted further, the screw-threaded portion 12 at the distal end of shaft 9 engages with the distal ends 30b, 31b of needles 30, 31 rotatably mounted in slots 23, 24 cut into upper side edges of the lower holding piece 20, which is affixed on the inside of the hollow tube 2 near the distal 7b, 8b of the longitudinal slots 7, 8.

As shown in FIG. 2(c), teeth 25 are also provided on inward facing arc portions 27 of distal ends 30b, 31b of the needles, the arc portions 27 having a predetermined length. The spaces 23, 24 are aligned to face the open longitudinal slots 7, 8 in the tube; in other words, the plane of the arc portions 27 of the distal ends of the needles passes through the longitudinal slots 7, 8 formed on opposite sides of the tube 2.

Again, during assembly of the medical instrument of the present invention, turnable shaft 9 is inserted into the tube 2 and through the upper and the lower cylindrical holding pieces 18 and 20. When inserted, shaft 9 is held in place with respect to the hollow tube by the cylindrical holding pieces 17, 18 and 19, 20 which fit snuggly around the shaft, and the teeth 25 of the arc portions 27 which engage with the screw threaded portion 12 of the shaft 9.

As described above and shown in FIG. 2(*b*), the distal ends 30*b*, 31*b* of the needles are rotatably mounted on pins 26 in slots 23, 24 cut into upper edges of holding piece 20. In an initial or closed position, the needles 30, 31 are arranged lengthwise along the length of the turnable shaft 9, and facing the open longitudinal slots 7, 8 of the hollow tube 2.

The length of the needles 30, 31 is in the range of 2 to 20 cm or 0.75 to 8 inches, preferably 2.5 to 7.5 cm or 1 to 3 inches. The length of the needles is less than the length of the open longitudinal slots, such that when the shaft 9 is turned by means of the knob 10, the proximal ends 30*a*, 31*a* of the needles radiate outwardly through the longitudinal slots 7, 8 for a predetermined distance, in the range of 0.5 to 2.0 cm By means of this turning, the needles 30, 31 can be positioned in either of two positions: a closed position (as shown in FIGS. 1 and 2), wherein the needles are pulled in close to the shaft 9, and an open position (as shown in FIG. 3), wherein the proximal ends of the needles project outward from shaft 9 for a predetermined distance as describe above. The predetermined distance by which the proximal ends 30*a*, 31*a* of the needles 30, 31 can rotate outwardly is limited by the length of arc portions 27 thereon. As shown in FIG. 2(*c*), a boss 28 is provided at the lower end of the arc portions 27 on the distal ends 30*b*, 31*b* of the needles. When the needles 30, 31 are rotated by a predetermined amount, bosses 28 press up against the shaft 9, and prevents further rotation of the needles.

As shown in FIG. 2 (*d*), eyes 30*e*, 31*e* are formed near the proximal ends 30*a*, 31*a* of each needle 30, 31, and each eye has a spring mechanism 30*s*, 31*s* for easy loading of the suture 40. Further, cutting tips 30*t*, 31*t* are formed at the tip of each needle.

A cylindrical seal member 35 is fitted around shaft 9 to form a tight seal the proximal end 2*b* of the hollow tube 2, for preventing gas from escaping from the operative surgical area 44.

Figure 6:
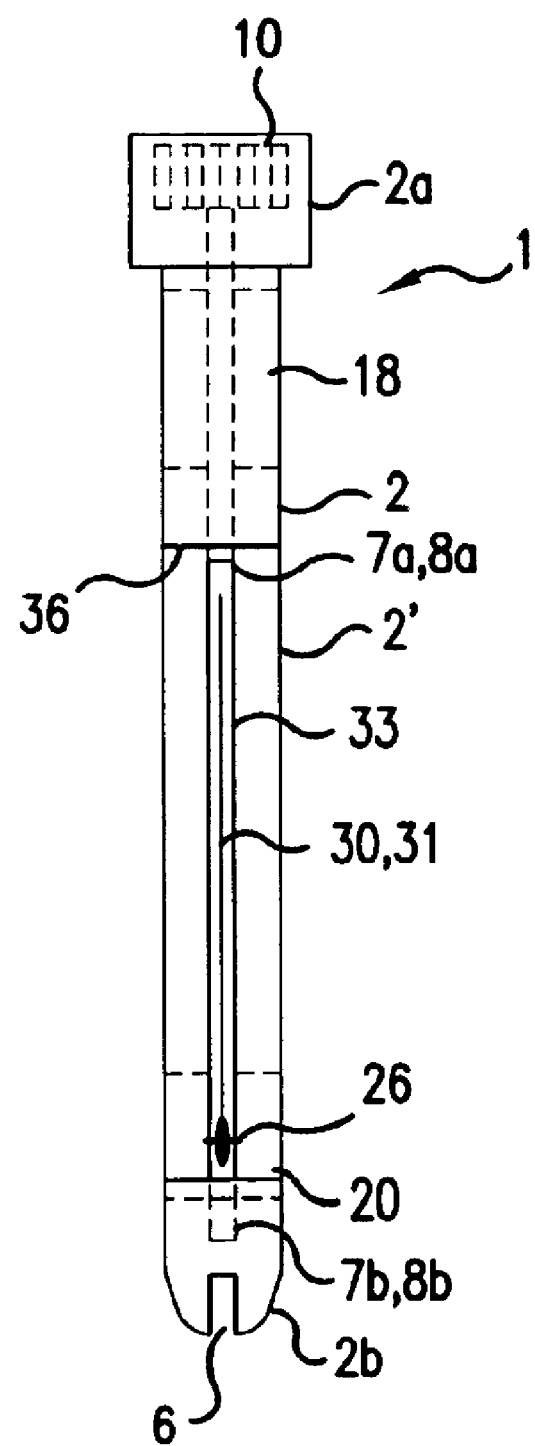
FIG. 6 is a sectional side view of a second embodiment of the present invention, similar to FIG. 1(b) above, and shows the niches which replace the slots of the hollow cylindrical member described in the first embodiment.

FIG. 6 shows a second embodiment of the present invention. In the second embodiment, the hollow cylindrical member 2 is provided with elongated niches 33 on the outer surface 2' of the cylindrical member 2, rather than longitudinal slots 7, 8 as described in the previous embodiment. In this second embodiment, the needles 30, 31 are rotatably mounted in the niches. When the needles are rotated, the proximal ends thereof project outwardly from the niches 33 to an open position similar to that described above in the previous embodiment.

Figure 7B:
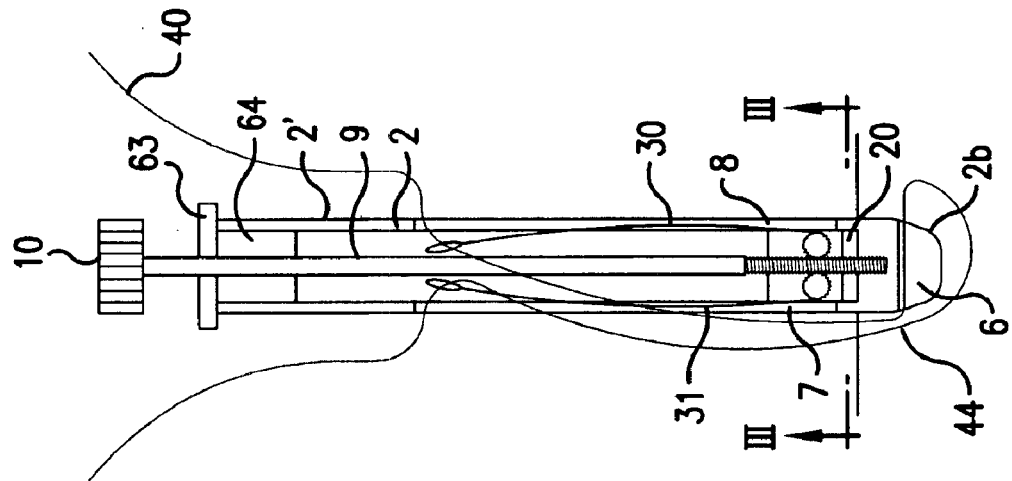
FIG. 7(b) is a sectional side view of the actuating mechanism subassembly after insertion into the hollow cylindrical member.
Figure 7A:
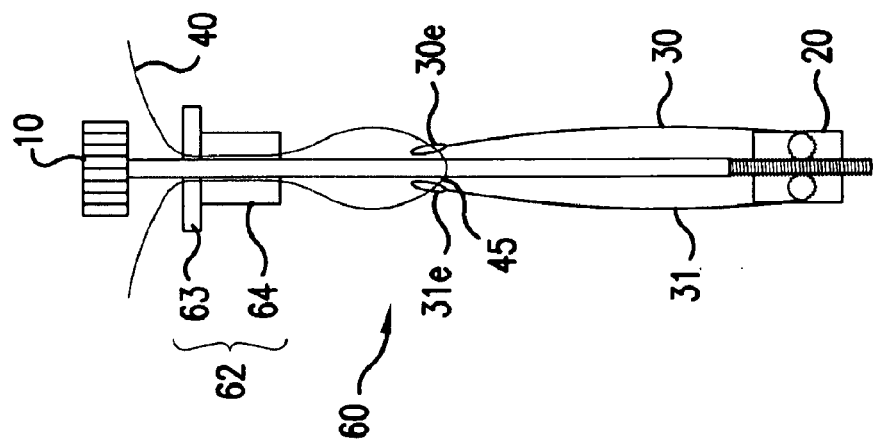
FIG. 7(a) is a side view of the actuating mechanism subassembly of the third embodiment of the present invention prior to insertion into the hollow cylindrical member.
Figure 8A:
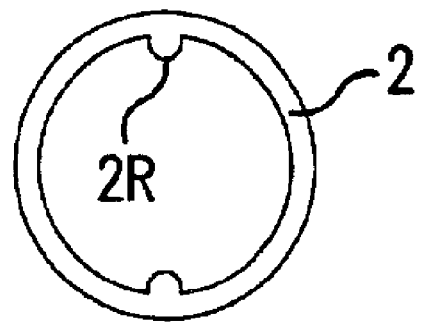
FIG. 8(a) shows a cross-sectional view of the cylindrical member.
Figure 8B:
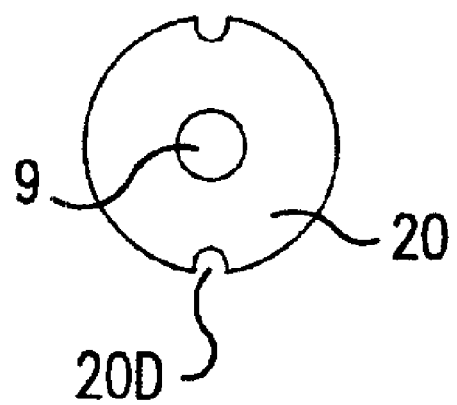
FIG. 8(b) shows a bottom face of the lower cylindrical holding piece that fits within the hollow cylindrical member, both FIGS. 8(a) and (b) being taken at line III—III of FIG. 7.

FIGS. 7(*a*) and (*b*), and FIGS. 8(*a*) and (*b*) show a third embodiment of the present invention. The third embodiment is similar to the first embodiment except that the actuating mechanism and needles 30, 31 are designed as a disposable subassembly 60 to be inserted as a unit into a reusable cylindrical member 2. Further, if desired, the needles may be pre-threaded with suture.

Actuating mechanism includes shaft 9, turnable knob 10, sealing member 62, and lower cylindrical holding piece 20. Needles 30, 31 are mounted and operate in the same manner as the needles in the first embodiment. Once the actuating mechanism and needles 30, 31 are inserted into cylindrical member 2, the configuration of the third embodiment is essentially the same as that of the first embodiment. Sealing member 62, which is integrally formed by cap 63 and fitting 64, is then pressed downward against the open end of the hollow cylindrical member 2 thus sealing the open end. At the same time, fitting 64 snuggly fits around shaft 9 stabilizing it within the proximal end of cylindrical member 2.

Cylindrical holding piece 20 surrounding the distal end of shaft 9 is formed with at least one groove 2D on an outer side thereof. The at least one groove 2D engages with at least one longitudinal ridge 2R projecting inwardly from the cylindrical member 2, and thus ensuring proper orientation of the needles with respect to longitudinal slots 7, 8.

In FIG. 7(*a*), suture 40 is shown forming a loop 45 as it passes through the eyes 30*e*, 31*e* of the needles. In FIG. 2(*b*), loop 45 of suture 40 is shown pulled downward from eyes 30*e*, 31*e*, out through longitudinal slots 7, 8 in cylindrical member 2, and down around the distal end 2*b*, where it is held in place in distal end slot 6.

Since the actuating mechanism and needles of the third embodiment described above are disposable, there is no need for these components to be cleansed and sterilized between uses, thus saving time and reducing possibility of contamination.

Figure 4:
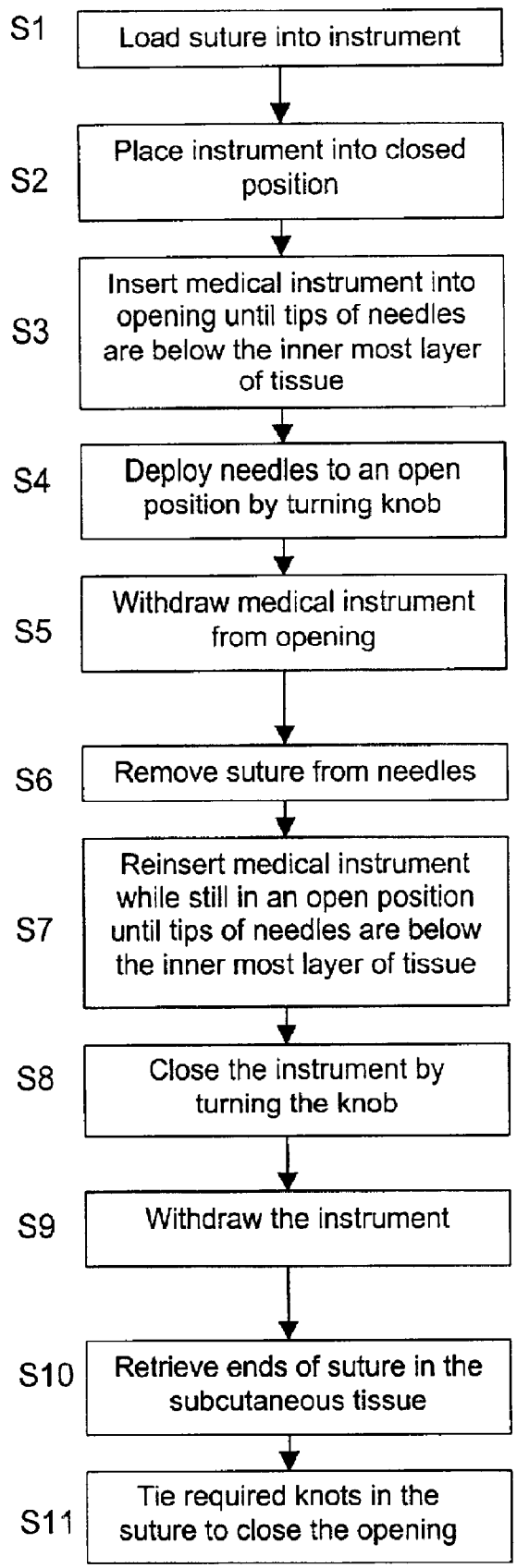
FIG. 4 is a flow chart of the steps of the method of closing a surgical opening with the instrument of the present invention.
Figure 5A:
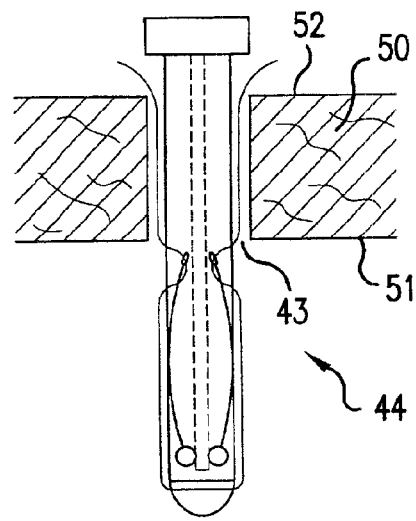
FIGS. 5(a)–5(e) are pictorial representations of steps S3, S4, S5, S9, and S11 of the method of closing a surgical opening using the instrument of the present invention.
Figure 5B:
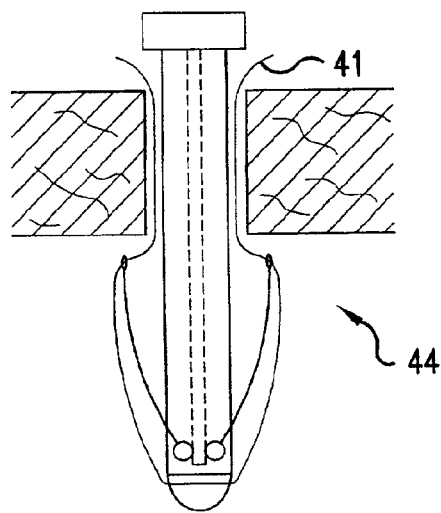
Figure 5C:
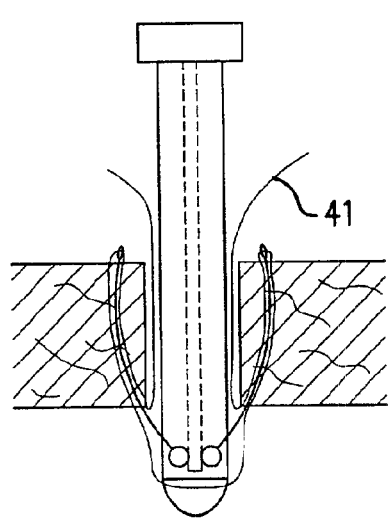
Figure 5D:
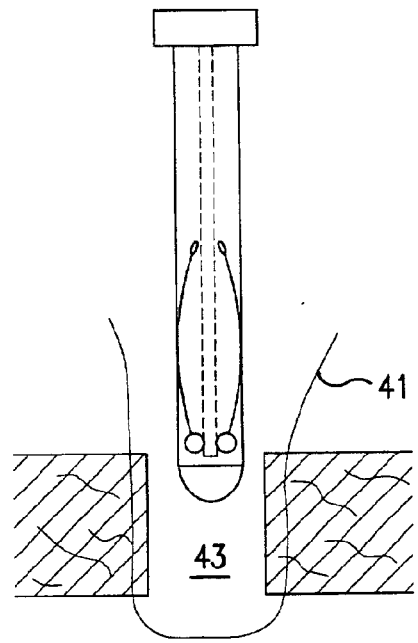
Figure 5E:
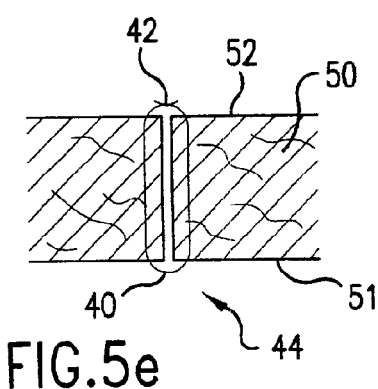

Next, is a description of the method steps involved in using the medical instrument of the present invention. These method steps are shown in FIGS. 4 and 5.

First, (Step S1), a length of suture 40 is threaded through the eye 30*e* of one needle 30, around the slot 6 at the distal end of the hollow cylindrical member or tube, and then through the eye 31*e* of the needle 31 on the opposite side of the cylindrical member. Once the suture 40 has been threaded through the needles 30, 31 and the distal end slot 6 as described, and the needles 30, 31 are placed in a closed position (Step S2), the instrument is ready for insertion (Step S3) into the surgical opening 43. The proper insertion depth is determined when mark 36 on the hollow cylindrical member is visible by the surgical viewing camera (not shown) and is determined to be inserted below the inner most layer 51 of tissue 50, and into the operative surgical area 44. This ensures that the proximal ends of the needles are lower than the inner most layer 51 of tissue 50, the knob on the shaft is turned (Step S4) to deploy the proximal end of the needles out through longitudinal slots 7, 8 to a predetermined distance from the outside of the cylindrical member. The distance of deployment of the needles 30, 31 is approximately 0.5 to 2 cm, and when the needles are so deployed, the instrument is in an open position. The instrument is then ready to be withdrawn from the opening 43. The instrument is withdrawn (Step S5) until the needles 30, 31 pierce through the layers of tissue 50 and for the tips 30*t*, 31*t* of the needles to emerge through the outer skin surface 52, whereby the suture 40 can be easily removed (Step S6) from the needle eyes 30*e*, 31*e*. The instrument, while still in its open position, is then reinserted (Step S7) into the opening 43 until the needle tips 30*t*, 31*t* are below the inner most layer 51. Next, (Step S8) the instrument is closed (needles 30*e*, 31*e* are retracted through longitudinal slots 7, 8 into a closed position), and the instrument is withdrawn from the opening 43 (Step S9). After this, the suture ends 41 are retrieved from below the skin level (in the subcutaneous tissue 50) (Step S10), and required knots 42 are tied to close the opening 43 (Step S11). The above procedure, results in the opening 43 being fastened at both the inner and outer layers 51, 52 of the tissue 50.

In the case of the third embodiment shown in FIGS. 7(*a*), 7(*b*), 8(*a*), and 8(*b*), the steps required to prepare the instrument are slightly different. With the actuating mechanism and needle subassembly 60, the suture is pre-threaded through the eyes of needles 30, 31 and up along the shaft 9 and through sealing member 62 as shown in FIG. 7(a). The subassembly 60 must first be inserted into cylinder member 2. Grooves 2R of holding member 20 engage with ridges 2R or the cylindrical member 2 causing the needles 30, 31 to be properly oriented with respect to longitudinal slots 7, 8.

Once the subassembly is inserted into the cylindrical member, loop 45 of suture 40 is then pulled out through one of longitudinal slots 7, 8 and down around slot 6 in the distal end 2b of the cylindrical member. Further, the upper ends of the suture are pulled out respectively through longitudinal slots 7, 8, causing the instrument to appear as shown in FIG. 7(b). This third embodiment is now ready for use as previously described in method steps S2–S11.

The invention being thus described, it will be obvious that the same may be varied in many ways. For example the instrument may be provided with more than the two needles described in the embodiment above. Further, the materials used to form the components described herein, may be metal, plastic, other suitable material, or combination of materials. Plastic components may be more suited for disposable components of the instruments, whereas metal components may be more suited for reusable components of the instruments. As described above, the needles of the medical instrument of the present invention may be formed with different lengths in order to accommodate the closing of surgical openings in tissues having different thicknesses. Further, the needles may be formed such that different types of suture may be used.

These and other variations are not to be regarded as a departure from the spirit and scope of the invention, and all such modifications as would be obvious to one skilled in the art are intended to be included within the scope of the following claims.

What is claimed is:

1. A medical instrument for closing an opening for surgery, comprising:

an elongated cylindrical member having an open proximal end and a closed distal end;

an actuating mechanism being operatively positioned within the cylindrical member;

at least two elongated needles secured to the cylindrical member and engaging with the actuating mechanism;

the at least two elongated needles include proximal ends capable of retaining a suture, the at least two needles being movable by the actuating mechanism from a closed position adjacent to an outer surface of the cylindrical member to an open position, wherein in the open position the proximal ends of the at least two needles extend away for the outer surface of the cylindrical member, wherein the cylindrical member is a hollow cylindrical member for containing the actuating mechanism, and wherein the actuating mechanism includes a shaft with a turntable knob at its proximal end and a screw threaded portion near its distal end for engaging with distal ends of the needles.

2. The medical instrument for closing an opening for surgery according to claim 1 wherein the hollow cylindrical member is a hollow tube for containing the at least two needles.

3. The medical instrument for closing an opening for surgery according to claim 2, wherein the hollow cylindrical member has an open longitudinal slot opposite each of the at least two needles, each of the needles being rotatably mounted at its distal end to the hollow cylindrical member and being rotatably deployed through the slots by the actuating mechanism.

4. The medical instrument for closing an opening for surgery according to claim 3, wherein the shaft of the actuating mechanism is held in place within the hollow cylindrical member by holding pieces securely fitting between the shaft and the hollow cylindrical member.

5. The medical instrument for closing an opening for surgery according to claim 1, wherein niches are formed at predetermined lengths on an outer surface of hollow cylindrical member for containing at the least two needles.

6. The medical instrument for closing an opening for surgery according to claim 1, wherein the hollow cylindrical member has a seal ring for preventing an escape of gases from the opening for surgery.

7. The medical instrument for closing an opening for surgery according to claim 1, wherein the needles have a length in the range of 2 to 20 cm or 0.75 to 8 inches.

8. The medical instrument for closing an opening for surgery according to claim 1, wherein the proximal ends of the needles project outwardly from the hollow cylindrical member by 0.5 to 2.0 cm when in an open position.

9. The medical instrument for closing an opening for surgery according to claim 1, wherein the actuating mechanism and the needles are formed as a subassembly for insertion into the hollow cylindrical member prior to using the medical instrument.

10. The medical instrument for closing an opening for surgery according to claim 1, wherein the hollow cylindrical member has at least one longitudinal ridge formed on its inner side for engaging with at least one groove formed on an outer side of a lower holding piece.

11. A method for closing a surgical opening employing a medical instrument having a cylindrical member, an actuating mechanism, and at least two elongated needles, the method comprising the steps of:

securing a suture to the at least two needles and to a distal end of the cylindrical member;

retracting the at least two needles, so that the at least two needles lie adjacent to an outer surface of the cylindrical member;

inserting the medical instrument until proximal ends of the at least two needles are below an inner most layer of tissue;

deploying needles to an open position;

withdrawing the medical instrument until the suture appears above the skin layer of a patient;

removing ends of the suture from the needles;

reinserting the medical instrument while still in an open position until the proximal ends of the at least two needles are below the inner most layer of tissue;

retracting the at least two needles so that needles are returned to a closed position and below the outer surface of the cylindrical member;

withdrawing the instrument;

retrieving ends of the suture in a subcutaneous tissue; and tying required knots in the suture, the knots closing the surgical opening, wherein the deploying step and the retracting step are accomplished by turning a knob on a proximal end of an elongated shaft of the actuating mechanism by a predetermined amount.

12. The method for closing a surgical opening employing a medical instrument according to claim 11, wherein the step of securing the suture includes passing the suture through a slot at the distal end of the cylindrical member.

13. The method for closing a surgical opening employing a medical instrument according to claim 11, wherein the needles have a length in the range of 2.0 to 20 cm or 0.75 to 8 inches.

14. The method for closing a surgical opening employing a medical instrument according to claim 11, wherein the cylindrical member has an open longitudinal slot opposite each of the at least two needles, each of the needles being rotatably mounted at its distal end to the cylindrical member and being rotatably deployed through the slots by the actuating mechanism.

15. The method for closing a surgical opening employing a medical instrument according to claim 11, wherein the cylindrical member is a hollow tube for containing the actuating mechanism and niches are formed at predetermined lengths on an outer surface of cylindrical member for containing the at least two needles.

16. The method for closing a surgical opening employing a medical instrument according to claim 11, wherein proximal ends of the needles project outwardly by 0.5 to 2.0 cm when deployed in the open position.

17. The method for closing a surgical opening employing a medical instrument according to claim 11, wherein the actuating mechanism and the needles are formed as a subassembly for insertion into the cylindrical member prior to using the medical instrument.

18. A medical instrument for closing an opening for surgery, comprising:

an elongated cylindrical member having an open proximal end and a closed distal end;

an actuating mechanism being operatively positioned within the elongated cylindrical member;

at least two elongated needles secured to the elongated cylindrical member and engaging with the actuating mechanism;

the at least two elongated needles including proximal ends capable of retaining a suture, the at least two needles being movable by the actuating mechanism from a closed position adjacent to an outer surface of the elongated cylindrical member to an open position, wherein in the open position the proximal ends of the at least two needles extend away from the outer surface of the cylindrical member, and wherein the elongated cylindrical member has at least one longitudinal ridge formed on its inner side for engaging with at least one groove formed on an outer side of a lower holding piece.

19. The medical instrument for closing an opening for surgery according to claim 18, wherein the elongated cylindrical member is a hollow tube for containing the actuating mechanism, and wherein the actuating mechanism includes a shaft with a turnable knob at its proximal and a screw threaded position near its distal end for engaging with the distal ends of the needles.

* * * * *